(12) United States Patent
Goodman et al.

(10) Patent No.: US 12,402,934 B2
(45) Date of Patent: Sep. 2, 2025

(54) ELECTROSURGICAL INSTRUMENT FOR GRASPING, TREATING, AND/OR DIVIDING TISSUE INCORPORATING THERMAL MANAGEMENT FEATURE

(71) Applicant: Covidien LP, Mansfield, MA (US)

(72) Inventors: Kelley D. Goodman, Erie, CO (US);
Craig V. Krastins, Arvada, CO (US);
Grant T. Sims, Boulder, CO (US);
Daniel W. Mercier, Erie, CO (US);
Jennifer L. Rich, Parker, CO (US)

(73) Assignee: Covidien LP, Mansfield, MA (US)

( * ) Notice: Subject to any disclaimer, the term of this patent is extended or adjusted under 35 U.S.C. 154(b) by 490 days.

(21) Appl. No.: 17/014,002

(22) Filed: Sep. 8, 2020

(65) Prior Publication Data

US 2021/0077178 A1 Mar. 18, 2021

Related U.S. Application Data

(60) Provisional application No. 62/900,573, filed on Sep. 15, 2019.

(51) Int. Cl.
*A61B 18/14* (2006.01)
*A61B 18/00* (2006.01)

(52) U.S. Cl.
CPC .............. *A61B 18/1442* (2013.01); *A61B 2018/00023* (2013.01); *A61B 2018/00077* (2013.01); *A61B 2018/00589* (2013.01); *A61B 2018/00595* (2013.01); *A61B 2018/0063* (2013.01)

(58) Field of Classification Search
CPC .......... A61B 2018/00023; A61B 2018/00077; A61B 18/1442
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| 4,763,669 A | 8/1988 | Jaeger |
| D298,353 S | 11/1988 | Manno |

(Continued)

FOREIGN PATENT DOCUMENTS

| | | |
|---|---|---|
| EP | 0246350 A1 | 11/1987 |
| WO | 2012116957 A1 | 9/2012 |

*Primary Examiner* — Joseph A Stoklosa
*Assistant Examiner* — Annie L Shoulders

(57) ABSTRACT

An electrosurgical instrument includes at least one shaft member, an end effector assembly extending distally from the at least one shaft member, and a heat pipe. The end effector assembly includes first and second jaw members, each including an electrically-conductive tissue-contacting surface. At least one of the first or second jaw members is movable relative to the other about a pivot between a spaced-apart position and an approximated position for grasping tissue between the electrically-conductive tissue-contacting surfaces. The heat pipe includes a proximal body portion and a flattened distal portion. The proximal body portion extends through at least a portion of the at least one shaft member, and the flattened distal portion extends through at least a portion of the first jaw member. The heat pipe is configured to facilitate drawing heat proximally from the end effector assembly.

20 Claims, 6 Drawing Sheets

(56) References Cited

U.S. PATENT DOCUMENTS

| | | |
|---|---|---|
| D299,413 S | 1/1989 | DeCarolis |
| 5,100,420 A | 3/1992 | Green et al. |
| 5,258,001 A | 11/1993 | Corman |
| D343,453 S | 1/1994 | Noda |
| 5,304,203 A | 4/1994 | El-Mallawany et al. |
| D348,930 S | 7/1994 | Olson |
| D349,341 S | 8/1994 | Lichtman et al. |
| 5,344,424 A | 9/1994 | Roberts et al. |
| D354,564 S | 1/1995 | Medema |
| D358,887 S | 5/1995 | Feinberg |
| 5,540,685 A | 7/1996 | Parins et al. |
| 5,578,052 A | 11/1996 | Koros et al. |
| 5,611,808 A | 3/1997 | Hossain et al. |
| 5,618,294 A | 4/1997 | Aust et al. |
| D384,413 S | 9/1997 | Zlock et al. |
| 5,665,100 A | 9/1997 | Yoon |
| 5,752,644 A | 5/1998 | Bolanos et al. |
| H1745 H | 8/1998 | Paraschac |
| 5,814,043 A | 9/1998 | Shapeton |
| D402,028 S | 12/1998 | Grimm et al. |
| D408,018 S | 4/1999 | McNaughton |
| 5,913,874 A | 6/1999 | Berns et al. |
| 5,960,544 A | 10/1999 | Beyers |
| D416,089 S | 11/1999 | Barton et al. |
| 6,050,996 A | 4/2000 | Schmaltz et al. |
| D424,694 S | 5/2000 | Tetzlaff et al. |
| D425,201 S | 5/2000 | Tetzlaff et al. |
| H1904 H | 10/2000 | Yates et al. |
| 6,293,954 B1 | 9/2001 | Fogarty et al. |
| D449,886 S | 10/2001 | Tetzlaff et al. |
| 6,329,778 B1 | 12/2001 | Culp et al. |
| 6,334,861 B1 | 1/2002 | Chandler et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| 6,406,485 B1 | 6/2002 | Hossain et al. |
| H2037 H | 7/2002 | Yates et al. |
| 6,464,704 B2 | 10/2002 | Schmaltz et al. |
| D465,281 S | 11/2002 | Lang |
| D466,209 S | 11/2002 | Bon |
| 6,511,480 B1 | 1/2003 | Tetzlaff et al. |
| 6,673,092 B1 | 1/2004 | Bacher |
| D493,888 S | 8/2004 | Reschke |
| D496,997 S | 10/2004 | Dycus et al. |
| 6,800,077 B1 * | 10/2004 | Mucko .............. A61B 18/1442 606/51 |
| D499,181 S | 11/2004 | Dycus et al. |
| D502,994 S | 3/2005 | Blake, III |
| D509,297 S | 9/2005 | Wells |
| 6,942,662 B2 * | 9/2005 | Goble .............. A61B 18/1402 606/50 |
| D525,361 S | 7/2006 | Hushka |
| 7,103,947 B2 | 9/2006 | Sartor et al. |
| D531,311 S | 10/2006 | Guerra et al. |
| 7,118,570 B2 | 10/2006 | Tetzlaff et al. |
| D533,274 S | 12/2006 | Visconti et al. |
| D533,942 S | 12/2006 | Kerr et al. |
| 7,147,638 B2 | 12/2006 | Chapman et al. |
| D535,027 S | 1/2007 | James et al. |
| 7,169,146 B2 | 1/2007 | Truckai et al. |
| D538,932 S | 3/2007 | Malik |
| D541,418 S | 4/2007 | Schechter et al. |
| D541,611 S | 5/2007 | Aglassinge |
| D541,938 S | 5/2007 | Kerr et al. |
| 7,220,951 B2 | 5/2007 | Truckai et al. |
| D545,432 S | 6/2007 | Watanabe |
| D547,154 S | 7/2007 | Lee |
| 7,329,257 B2 | 2/2008 | Kanehira et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| 7,431,730 B2 | 10/2008 | Viola |
| D582,038 S | 12/2008 | Swoyer et al. |
| 7,641,653 B2 | 1/2010 | Dalla Betta et al. |
| 7,708,735 B2 | 5/2010 | Chapman et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| 7,854,185 B2 | 12/2010 | Zhang et al. |
| D630,324 S | 1/2011 | Reschke |
| 7,896,878 B2 | 3/2011 | Johnson et al. |
| D649,249 S | 11/2011 | Guerra |
| D649,643 S | 11/2011 | Allen, IV et al. |
| 8,100,894 B2 * | 1/2012 | Mucko .............. A61B 18/1442 606/51 |
| 8,147,489 B2 | 4/2012 | Moses et al. |
| D661,394 S | 6/2012 | Romero et al. |
| 8,292,880 B2 * | 10/2012 | Prakash .............. A61B 18/1815 606/41 |
| 8,298,233 B2 | 10/2012 | Mueller |
| D670,808 S | 11/2012 | Moua et al. |
| 8,366,709 B2 | 2/2013 | Schechter et al. |
| 8,394,096 B2 | 3/2013 | Moses et al. |
| D680,220 S | 4/2013 | Rachlin |
| 8,409,246 B2 | 4/2013 | Kerr et al. |
| 8,409,247 B2 | 4/2013 | Garrison et al. |
| 8,425,504 B2 | 4/2013 | Orton et al. |
| 8,425,511 B2 | 4/2013 | Olson |
| 8,430,877 B2 | 4/2013 | Kerr et al. |
| 8,439,913 B2 | 5/2013 | Horner et al. |
| 8,469,716 B2 | 6/2013 | Fedotov et al. |
| 8,469,991 B2 | 6/2013 | Kerr |
| 8,469,992 B2 | 6/2013 | Roy et al. |
| 8,480,671 B2 | 7/2013 | Mueller |
| 8,491,624 B2 | 7/2013 | Kerr et al. |
| 8,491,625 B2 | 7/2013 | Horner |
| 8,491,626 B2 | 7/2013 | Roy et al. |
| 8,512,336 B2 | 8/2013 | Couture |
| 8,540,749 B2 | 9/2013 | Garrison et al. |
| 8,551,091 B2 | 10/2013 | Couture et al. |
| 8,556,929 B2 | 10/2013 | Harper et al. |
| 8,568,397 B2 | 10/2013 | Horner et al. |
| 8,568,408 B2 | 10/2013 | Townsend et al. |
| 8,585,736 B2 | 11/2013 | Horner et al. |
| 8,591,510 B2 | 11/2013 | Allen, IV et al. |
| 8,597,295 B2 | 12/2013 | Kerr |
| 8,623,018 B2 | 1/2014 | Horner et al. |
| 8,628,557 B2 | 1/2014 | Collings et al. |
| 8,641,712 B2 | 2/2014 | Couture |
| 8,647,343 B2 | 2/2014 | Chojin et al. |
| 8,652,135 B2 | 2/2014 | Nau, Jr. |
| 8,663,222 B2 | 3/2014 | Anderson et al. |
| 8,672,939 B2 | 3/2014 | Garrison |
| 8,679,098 B2 | 3/2014 | Hart |
| 8,685,009 B2 | 4/2014 | Chernov et al. |
| 8,685,021 B2 | 4/2014 | Chernov et al. |
| 8,685,056 B2 | 4/2014 | Evans et al. |
| 8,702,737 B2 | 4/2014 | Chojin et al. |
| 8,702,749 B2 | 4/2014 | Twomey |
| 8,734,445 B2 | 5/2014 | Johnson et al. |
| 8,740,898 B2 | 6/2014 | Chojin et al. |
| 8,745,840 B2 | 6/2014 | Hempstead et al. |
| 8,747,434 B2 | 6/2014 | Larson et al. |
| 8,756,785 B2 | 6/2014 | Allen, IV et al. |
| 8,784,418 B2 | 7/2014 | Romero |
| 8,795,269 B2 | 8/2014 | Garrison |
| 8,808,288 B2 | 8/2014 | Reschke |
| 8,814,864 B2 | 8/2014 | Gilbert |
| 8,840,639 B2 | 9/2014 | Gerhardt, Jr. et al. |
| 8,845,636 B2 | 9/2014 | Allen, IV et al. |
| 8,852,185 B2 | 10/2014 | Twomey |
| 8,852,228 B2 | 10/2014 | Nau, Jr. |
| 8,858,553 B2 | 10/2014 | Chojin |
| 8,864,753 B2 | 10/2014 | Nau, Jr. et al. |
| 8,864,795 B2 | 10/2014 | Kerr et al. |
| 8,887,373 B2 | 11/2014 | Brandt et al. |

(56) References Cited

U.S. PATENT DOCUMENTS

| | | |
|---|---|---|
| 8,888,771 B2 | 11/2014 | Twomey |
| 8,888,775 B2 | 11/2014 | Nau, Jr. et al. |
| 8,898,888 B2 | 12/2014 | Brandt et al. |
| 8,900,232 B2 | 12/2014 | Ourada |
| 8,906,018 B2 | 12/2014 | Rooks et al. |
| 8,920,421 B2 | 12/2014 | Rupp |
| 8,932,293 B2 | 1/2015 | Chernov et al. |
| 8,936,614 B2 | 1/2015 | Allen, IV |
| 8,939,972 B2 | 1/2015 | Twomey |
| 8,945,175 B2 | 2/2015 | Twomey |
| 8,961,504 B2 | 2/2015 | Hoarau et al. |
| 8,968,283 B2 | 3/2015 | Kharin |
| 8,968,305 B2 | 3/2015 | Dumbauld et al. |
| 8,968,316 B2 | 3/2015 | Roy et al. |
| 8,968,357 B2 | 3/2015 | Mueller |
| 8,968,359 B2 | 3/2015 | Kerr et al. |
| 9,005,200 B2 | 4/2015 | Roy et al. |
| 9,017,372 B2 | 4/2015 | Artale et al. |
| 9,028,484 B2 | 5/2015 | Craig |
| 9,028,492 B2 | 5/2015 | Kerr et al. |
| 9,028,495 B2 | 5/2015 | Mueller et al. |
| 9,039,704 B2 | 5/2015 | Joseph |
| 9,039,732 B2 | 5/2015 | Sims et al. |
| 9,084,608 B2 | 7/2015 | Larson et al. |
| 9,113,933 B2 | 8/2015 | Chernova et al. |
| 9,113,934 B2 | 8/2015 | Chernov et al. |
| 9,161,807 B2 | 10/2015 | Garrison |
| 9,211,657 B2 | 12/2015 | Ackley et al. |
| 9,265,565 B2 | 2/2016 | Kerr |
| 9,265,568 B2 | 2/2016 | Chernov et al. |
| 9,333,002 B2 | 5/2016 | Garrison |
| 9,381,059 B2 | 7/2016 | Garrison |
| 9,439,710 B2 | 9/2016 | Reu et al. |
| 9,456,870 B2 | 10/2016 | Chernov et al. |
| 9,498,278 B2 | 11/2016 | Couture et al. |
| 9,498,279 B2 | 11/2016 | Artale et al. |
| 9,504,519 B2 | 11/2016 | Kerr et al. |
| 9,585,709 B2 | 3/2017 | Krapohl |
| 9,615,877 B2 | 4/2017 | Tyrrell et al. |
| 9,655,672 B2 | 5/2017 | Artale et al. |
| 9,962,221 B2 | 5/2018 | Lee et al. |
| 9,987,078 B2 | 6/2018 | Thomson et al. |
| 2002/0016591 A1* | 2/2002 | Levine ............... A61B 18/1442 606/51 |
| 2003/0018332 A1 | 1/2003 | Schmaltz et al. |
| 2003/0109875 A1 | 6/2003 | Tetzlaff et al. |
| 2003/0199869 A1 | 10/2003 | Johnson et al. |
| 2003/0220637 A1 | 11/2003 | Truckai et al. |
| 2003/0229344 A1 | 12/2003 | Dycus et al. |
| 2004/0092927 A1 | 5/2004 | Podhajsky et al. |
| 2005/0070889 A1 | 3/2005 | Nobis et al. |
| 2005/0107784 A1 | 5/2005 | Moses et al. |
| 2005/0113826 A1 | 5/2005 | Johnson et al. |
| 2005/0113828 A1 | 5/2005 | Shields et al. |
| 2005/0159745 A1 | 7/2005 | Truckai et al. |
| 2006/0253126 A1 | 11/2006 | Bjerken et al. |
| 2007/0062017 A1 | 3/2007 | Dycus et al. |
| 2007/0088356 A1 | 4/2007 | Moses et al. |
| 2007/0179499 A1 | 8/2007 | Garrison |
| 2007/0260241 A1 | 11/2007 | Dalla Betta et al. |
| 2008/0215048 A1 | 9/2008 | Hafner et al. |
| 2009/0131934 A1 | 5/2009 | Odom et al. |
| 2009/0171353 A1 | 7/2009 | Johnson et al. |
| 2009/0182327 A1 | 7/2009 | Unger |
| 2009/0240246 A1 | 9/2009 | Deville et al. |
| 2009/0302090 A1 | 12/2009 | Shah |
| 2009/0308909 A1 | 12/2009 | Nalagatla et al. |
| 2010/0016857 A1 | 1/2010 | McKenna et al. |
| 2010/0130977 A1 | 5/2010 | Garrison et al. |
| 2010/0179545 A1 | 7/2010 | Twomey et al. |
| 2010/0179547 A1 | 7/2010 | Cunningham et al. |
| 2010/0228250 A1 | 9/2010 | Brogna |
| 2010/0274244 A1 | 10/2010 | Heard |
| 2010/0292691 A1 | 11/2010 | Brogna |
| 2010/0305567 A1 | 12/2010 | Swanson |
| 2011/0054469 A1 | 3/2011 | Kappus et al. |
| 2011/0060314 A1 | 3/2011 | Wallace et al. |
| 2011/0060356 A1 | 3/2011 | Reschke et al. |
| 2011/0072638 A1 | 3/2011 | Brandt et al. |
| 2011/0087218 A1 | 4/2011 | Boudreaux et al. |
| 2011/0218530 A1 | 9/2011 | Reschke |
| 2011/0238065 A1 | 9/2011 | Hunt et al. |
| 2011/0238067 A1 | 9/2011 | Moses et al. |
| 2011/0257680 A1 | 10/2011 | Reschke et al. |
| 2011/0270245 A1 | 11/2011 | Horner et al. |
| 2011/0270251 A1 | 11/2011 | Horner et al. |
| 2011/0276049 A1 | 11/2011 | Gerhardt |
| 2011/0295313 A1 | 12/2011 | Kerr |
| 2012/0059372 A1 | 3/2012 | Johnson |
| 2012/0059409 A1 | 3/2012 | Reschke et al. |
| 2012/0083785 A1 | 4/2012 | Roy et al. |
| 2012/0083786 A1 | 4/2012 | Artale et al. |
| 2012/0083827 A1 | 4/2012 | Artale et al. |
| 2012/0123402 A1 | 5/2012 | Chernov et al. |
| 2012/0123404 A1 | 5/2012 | Craig |
| 2012/0123410 A1 | 5/2012 | Craig |
| 2012/0130367 A1 | 5/2012 | Garrison |
| 2012/0136354 A1 | 5/2012 | Rupp |
| 2012/0172868 A1 | 7/2012 | Twomey et al. |
| 2012/0172873 A1 | 7/2012 | Artale et al. |
| 2012/0172924 A1 | 7/2012 | Allen, IV |
| 2012/0184988 A1 | 7/2012 | Twomey et al. |
| 2012/0184989 A1 | 7/2012 | Twomey |
| 2012/0184990 A1 | 7/2012 | Twomey |
| 2012/0209263 A1 | 8/2012 | Sharp et al. |
| 2012/0215219 A1 | 8/2012 | Roy et al. |
| 2012/0239034 A1 | 9/2012 | Horner et al. |
| 2012/0253344 A1 | 10/2012 | Dumbauld et al. |
| 2012/0259331 A1 | 10/2012 | Garrison |
| 2012/0265241 A1 | 10/2012 | Hart et al. |
| 2012/0283727 A1 | 11/2012 | Twomey |
| 2012/0296205 A1 | 11/2012 | Chernov et al. |
| 2012/0296238 A1 | 11/2012 | Chernov et al. |
| 2012/0296239 A1 | 11/2012 | Chernov et al. |
| 2012/0296317 A1 | 11/2012 | Chernov et al. |
| 2012/0296323 A1 | 11/2012 | Chernov et al. |
| 2012/0296324 A1 | 11/2012 | Chernov et al. |
| 2012/0296334 A1 | 11/2012 | Kharin |
| 2012/0303025 A1 | 11/2012 | Garrison |
| 2012/0323238 A1 | 12/2012 | Tyrrell et al. |
| 2012/0330308 A1 | 12/2012 | Joseph |
| 2012/0330309 A1 | 12/2012 | Joseph |
| 2013/0018364 A1 | 1/2013 | Chernov et al. |
| 2013/0018372 A1 | 1/2013 | Sims et al. |
| 2013/0018411 A1 | 1/2013 | Collings et al. |
| 2013/0022495 A1 | 1/2013 | Allen, IV et al. |
| 2013/0030432 A1 | 1/2013 | Garrison et al. |
| 2013/0041370 A1 | 2/2013 | Unger |
| 2013/0046295 A1 | 2/2013 | Kerr et al. |
| 2013/0046303 A1 | 2/2013 | Evans et al. |
| 2013/0046306 A1 | 2/2013 | Evans et al. |
| 2013/0046337 A1 | 2/2013 | Evans et al. |
| 2013/0060250 A1 | 3/2013 | Twomey et al. |
| 2013/0066318 A1 | 3/2013 | Kerr |
| 2013/0071282 A1 | 3/2013 | Fry |
| 2013/0072927 A1 | 3/2013 | Allen, IV et al. |
| 2013/0079760 A1 | 3/2013 | Twomey et al. |
| 2013/0079762 A1 | 3/2013 | Twomey et al. |
| 2013/0079774 A1 | 3/2013 | Whitney et al. |
| 2013/0085491 A1 | 4/2013 | Twomey et al. |
| 2013/0085496 A1 | 4/2013 | Unger et al. |
| 2013/0103030 A1 | 4/2013 | Garrison |
| 2013/0103031 A1 | 4/2013 | Garrison |
| 2013/0103035 A1 | 4/2013 | Horner et al. |
| 2013/0123837 A1 | 5/2013 | Roy et al. |
| 2013/0138101 A1 | 5/2013 | Kerr |
| 2013/0138102 A1 | 5/2013 | Twomey et al. |
| 2013/0138129 A1 | 5/2013 | Garrison et al. |
| 2013/0144284 A1 | 6/2013 | Behnke et al. |
| 2013/0178852 A1 | 7/2013 | Allen, IV et al. |
| 2013/0185922 A1 | 7/2013 | Twomey et al. |
| 2013/0190753 A1 | 7/2013 | Garrison et al. |
| 2013/0190760 A1 | 7/2013 | Allen, IV et al. |
| 2013/0197503 A1 | 8/2013 | Orszulak |

(56) References Cited

U.S. PATENT DOCUMENTS

| | | |
|---|---|---|
| 2013/0226177 A1 | 8/2013 | Brandt et al. |
| 2014/0221994 A1 | 8/2014 | Reschke |
| 2014/0221995 A1 | 8/2014 | Guerra et al. |
| 2014/0221999 A1 | 8/2014 | Cunningham et al. |
| 2014/0228842 A1 | 8/2014 | Dycus et al. |
| 2014/0230243 A1 | 8/2014 | Roy et al. |
| 2014/0236149 A1 | 8/2014 | Kharin et al. |
| 2014/0243811 A1 | 8/2014 | Reschke et al. |
| 2014/0243824 A1 | 8/2014 | Gilbert |
| 2014/0249528 A1 | 9/2014 | Hixson et al. |
| 2014/0250686 A1 | 9/2014 | Hempstead et al. |
| 2014/0257274 A1 | 9/2014 | McCullough, Jr. et al. |
| 2014/0257283 A1 | 9/2014 | Johnson et al. |
| 2014/0257284 A1 | 9/2014 | Artale |
| 2014/0257285 A1 | 9/2014 | Moua |
| 2014/0276803 A1 | 9/2014 | Hart |
| 2014/0284313 A1 | 9/2014 | Allen, IV et al. |
| 2014/0288549 A1 | 9/2014 | McKenna et al. |
| 2014/0288553 A1 | 9/2014 | Johnson et al. |
| 2014/0330308 A1 | 11/2014 | Hart et al. |
| 2014/0336635 A1 | 11/2014 | Hart et al. |
| 2014/0353188 A1 | 12/2014 | Reschke et al. |
| 2015/0018816 A1 | 1/2015 | Latimer |
| 2015/0025528 A1 | 1/2015 | Arts |
| 2015/0032106 A1 | 1/2015 | Rachlin |
| 2015/0051598 A1 | 2/2015 | Orszulak et al. |
| 2015/0051640 A1 | 2/2015 | Twomey et al. |
| 2015/0066026 A1 | 3/2015 | Hart et al. |
| 2015/0066076 A1 | 3/2015 | Kerr et al. |
| 2015/0080889 A1 | 3/2015 | Cunningham et al. |
| 2015/0082928 A1 | 3/2015 | Kappus et al. |
| 2015/0088122 A1 | 3/2015 | Jensen |
| 2015/0088126 A1 | 3/2015 | Duffin et al. |
| 2015/0088128 A1 | 3/2015 | Couture |
| 2015/0094714 A1 | 4/2015 | Lee et al. |
| 2016/0157925 A1 | 6/2016 | Artale et al. |
| 2016/0175031 A1 | 6/2016 | Boudreaux |
| 2017/0128120 A1 | 5/2017 | Cho et al. |
| 2018/0199986 A1* | 7/2018 | Ding .......... A61B 18/1445 |
| 2018/0353162 A1 | 12/2018 | Hancock et al. |
| 2018/0368910 A1* | 12/2018 | Kirwan, Jr. ...... A61B 18/1445 |

* cited by examiner

ELECTROSURGICAL INSTRUMENT FOR GRASPING, TREATING, AND/OR DIVIDING TISSUE INCORPORATING THERMAL MANAGEMENT FEATURE

CROSS-REFERENCE TO RELATED APPLICATIONS

This application claims the benefit of, and priority to, U.S. Provisional Patent Application No. 62/900,573, filed on Sep. 15, 2019, the entire contents of which are hereby incorporated by reference herein.

FIELD

The present disclosure relates to electrosurgical instruments and, more particularly, to an electrosurgical instrument for grasping, treating, and/or dividing tissue that incorporates a thermal management feature.

BACKGROUND

A surgical forceps is a plier-like instrument which relies on mechanical action between its jaws to grasp tissue. Electrosurgical forceps utilize both mechanical clamping action and electrical energy to treat tissue, e.g., coagulate, cauterize, and/or seal tissue.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is an electrosurgical instrument. The electrosurgical instrument includes at least one shaft member. In aspects, the electrosurgical instrument includes first and second shaft members. An end effector assembly extends distally from the at least one shaft member. The end effector assembly includes first and second jaw members, each including an electrically-conductive tissue-contacting surface. At least one of the first or second jaw members is movable relative to the other about a pivot between a spaced-apart position and an approximated position for grasping tissue between the electrically-conductive tissue-contacting surfaces. In aspects where the electrosurgical instrument includes first and second shaft members, the first and second shaft members are movable about the pivot and relative to one another between an open position and a closed position to move the first or second jaw members between the spaced-apart position and the approximated position.

The electrosurgical instrument further includes a heat pipe including a proximal body portion and a flattened distal portion. The proximal body portion extending through at least a portion of the at least one shaft member (the first shaft member, in aspects where first and second shaft members are provided), and the flattened distal portion extends through at least a portion of the first jaw member. The heat pipe is configured to facilitate drawing heat proximally from the first and second jaw members.

In an aspect of the present disclosure, the heat pipe defines an internal lumen extending therethrough. The internal lumen is, in aspects, partially constricted and, in other aspects, fully constricted, in the distal flattened portion of the heat pipe.

In another aspect of the present disclosure, the distal flattened portion of the heat pipe defines a spatula-shaped configuration.

In still another aspect of the present disclosure, the distal flattened portion of the heat pipe includes an upper surface defining a plane disposed in parallel orientation relative to a plane defined by the electrically-conductive tissue-contacting surface of the first jaw member.

In yet another aspect of the present disclosure, the heat pipe includes a cooling fluid disposed therein.

In still yet another aspect of the present disclosure, the at least one shaft member (the first shaft member) includes an inner frame and an outer housing. The proximal body portion of the heat pipe extends through the outer housing and at least one of: alongside, above, below, or through the inner frame.

In another aspect of the present disclosure, a length of the distal flattened portion of the heat pipe is configured in accordance with a length of the electrically-conductive tissue-contacting surface of the first jaw member. Additionally or alternatively, a length of the heat pipe is configured in accordance with a length of the electrically-conductive tissue-contacting surface of the first jaw member. Further still, as an addition or alternative, a cross-sectional area of the heat pipe may be configured in accordance with an exposed surface area of the electrically-conductive tissue-contacting surface of the first jaw member.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements.

DETAILED DESCRIPTION

Figure 1A:
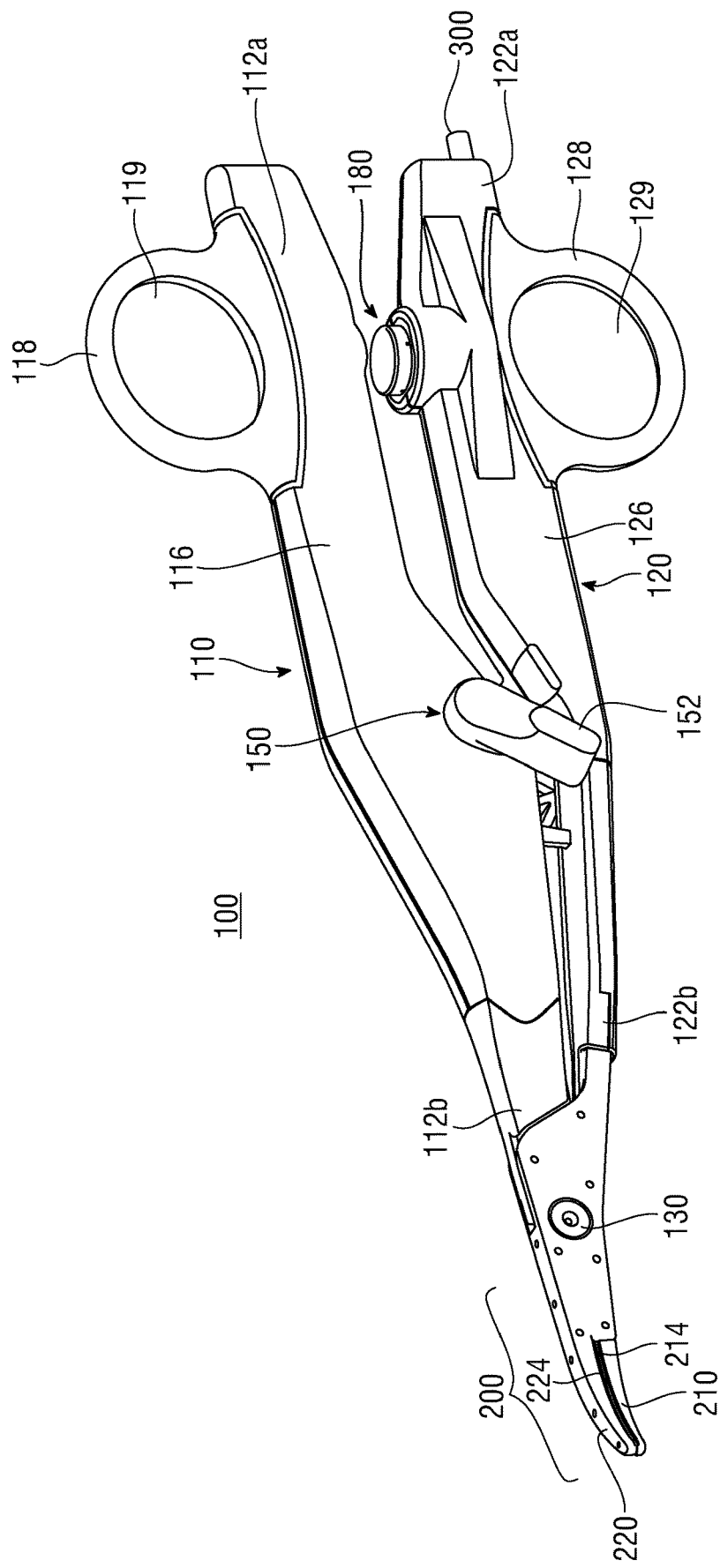
FIG. 1A is a perspective view, from a first side, of an electrosurgical instrument provided in accordance with aspects the present disclosure.
Figure 1B:
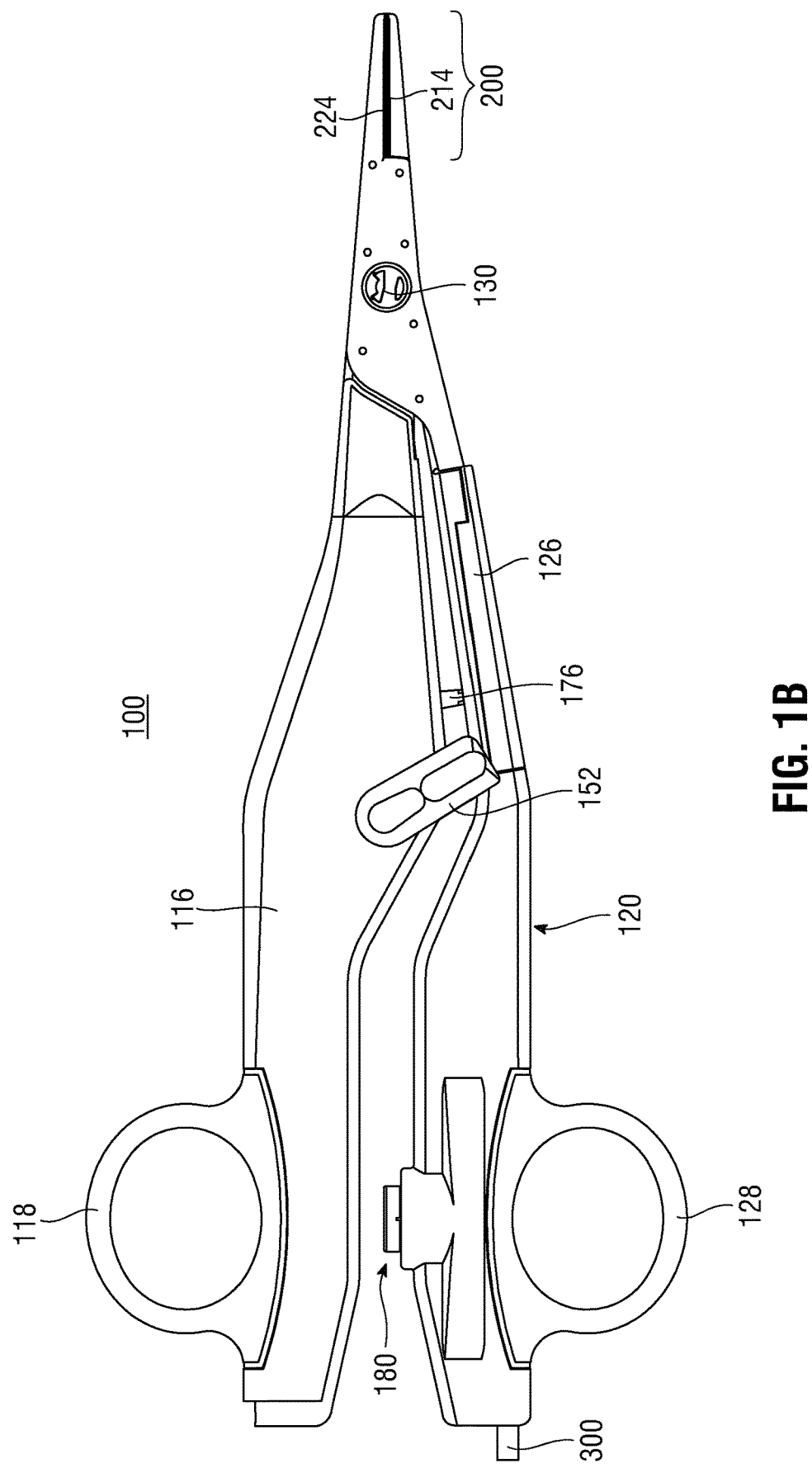
FIG. 1B is a side view, from a second, opposite side, of the electrosurgical instrument of FIG. 1A.

Referring to FIGS. 1A-2B, an electrosurgical instrument provided in accordance with the present disclosure is shown generally identified by reference numeral 100. Instrument 100 includes first and second shaft members 110, 120 each having a proximal end portion 112a, 122a and a distal end portion 112b, 122b. An end effector assembly 200 of instrument 100 includes first and second jaw members 210, 220 extending from distal end portions 112b, 122b of shaft members 110, 120, respectively. Instrument 100 further includes a pivot 130 pivotably coupling first and second shaft members 110, 120 with one another towards distal end portions 112b, 122b, respectively, thereof to enable pivoting of shaft members 110, 120 relative to one another between an open position and a closed position to thereby pivot jaw members 210, 220 relative to one another between a spaced-apart position and an approximated position to grasp tissue therebetween. Instrument 100 additionally includes a knife 140, a knife deployment mechanism 150 for selectively deploying knife 140 between jaw members 210, 220 of end effector assembly 200, a knife lockout mechanism 170 for inhibiting deployment of knife 140 prior to sufficient approximation of jaw members 210, 220, and a switch assembly 180 for enabling the selective supply of electrosurgical energy to end effector assembly 200. An electrosurgical cable 300 electrically couples instrument 100 to a source of energy (not shown), e.g., an electrosurgical generator, to enable the supply of electrosurgical energy to jaw members 210, 220 of end effector assembly 200 upon activation of switch assembly 180.

A thermal management feature in the form of a heat pipe 400 (FIGS. 3A-4) extends at least partially through one of the shaft members and the corresponding jaw member, e.g., shaft member 110 and jaw member 210, to facilitate drawing heat proximally away from end effector assembly 200, thus facilitating cooling of end effector assembly 200 after use, minimizing thermal spread during use, and/or reducing harm from accidental contact with end effector assembly 200 during or after use. Heat pipe 400 (FIGS. 3A-4) is described in greater detail below.

Although instrument 100 is illustrated and described herein as a hemostat-style electrosurgical instrument, other electrosurgical instruments such as shaft-based electrosurgical instruments, e.g., electrosurgical instruments including a housing, a shaft extending distally from housing, and end effector assembly 200 disposed at the distal end portion of the shaft; robotic electrosurgical instruments, e.g., electrosurgical instruments including a robotic attachment hub, a shaft extending distally from the attachment hub, and end effector assembly 200 disposed at the distal end portion of the shaft; or other suitable electrosurgical instruments are also contemplated and may include some or all of the features of instrument 100, e.g., heat pipe 400 (FIGS. 3A-4), detailed hereinbelow.

Continuing with reference to FIGS. 1A-2B, each shaft member 110, 120 includes an inner frame 114, 124, an outer housing 116, 126 surrounding at least a portion of the respective inner frame 114, 124, and a handle 118, 128 engaged with the respective outer housing 116, 126 towards the proximal end portion 112a, 122a of the respective shaft member 110, 120.

Inner frames 114, 124 support jaw members 210, 220, respectively, thereon at the distal ends thereof, provide structural support to shaft members 110, 120, and operably support the internal components disposed within shaft members 110, 120. Further, pivot 130 extends through pivot apertures defined within inner frames 114, 124 to pivotably couple shaft members 110, 120 with one another towards distal end portion 112b, 122b, respectively, thereof such that, as noted above, pivoting of shaft members 110, 120 relative to one another between the open and closed positions pivots jaw members 210, 220 relative to one another between the spaced-apart and approximated positions to grasp tissue therebetween. One or both of inner frames 114, 124 may be formed from one or more structures secured to one another. For example, inner frame 114 of shaft member 110 may include a body plate 115a and a reinforcing plate 115b attached to body plate 115a, e.g., via welding, to provide increased lateral stiffness and structural support thereto.

Outer housings 116, 126 of shaft members 110, 120 enclose and/or operably support the internal components disposed within shaft members 110, 120. More specifically, outer housing 116 of shaft member 110 encloses and supports at least a portion of inner frame 114, knife deployment mechanism 150, and knife lockout mechanism 170, while outer housing 126 of shaft member 120 receives electrosurgical cable 300 and encloses and supports at least a portion of inner frame 124, switch assembly 180, and the lead wires 310 of electrosurgical cable 300. Handles 118, 128 are engaged with outer housings 116, 126 towards proximal end portions 112a, 112b of shaft members 110, 120 and extend outwardly from shaft members 110, 120. Handles 118, 128 define finger holes 119, 129 configured to facilitate grasping and manipulating shaft members 110, 120, e.g., between the open and closed positions.

Figure 2A:
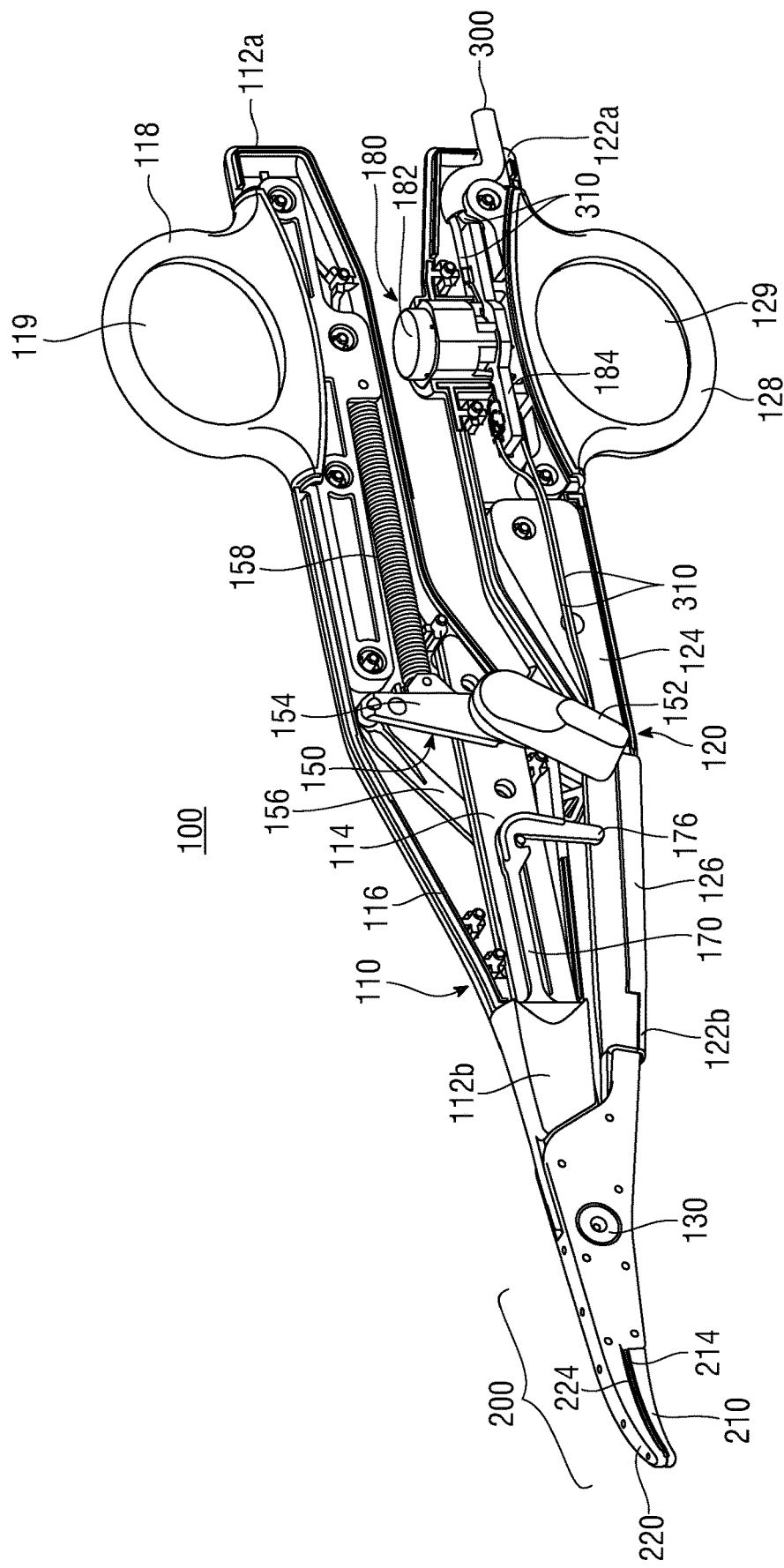
FIG. 2A is a perspective view, from the first side, of the electrosurgical instrument of FIG. 1A with portions of the outer housings of the first and second shaft members removed to illustrate the internal components therein.
Figure 2B:
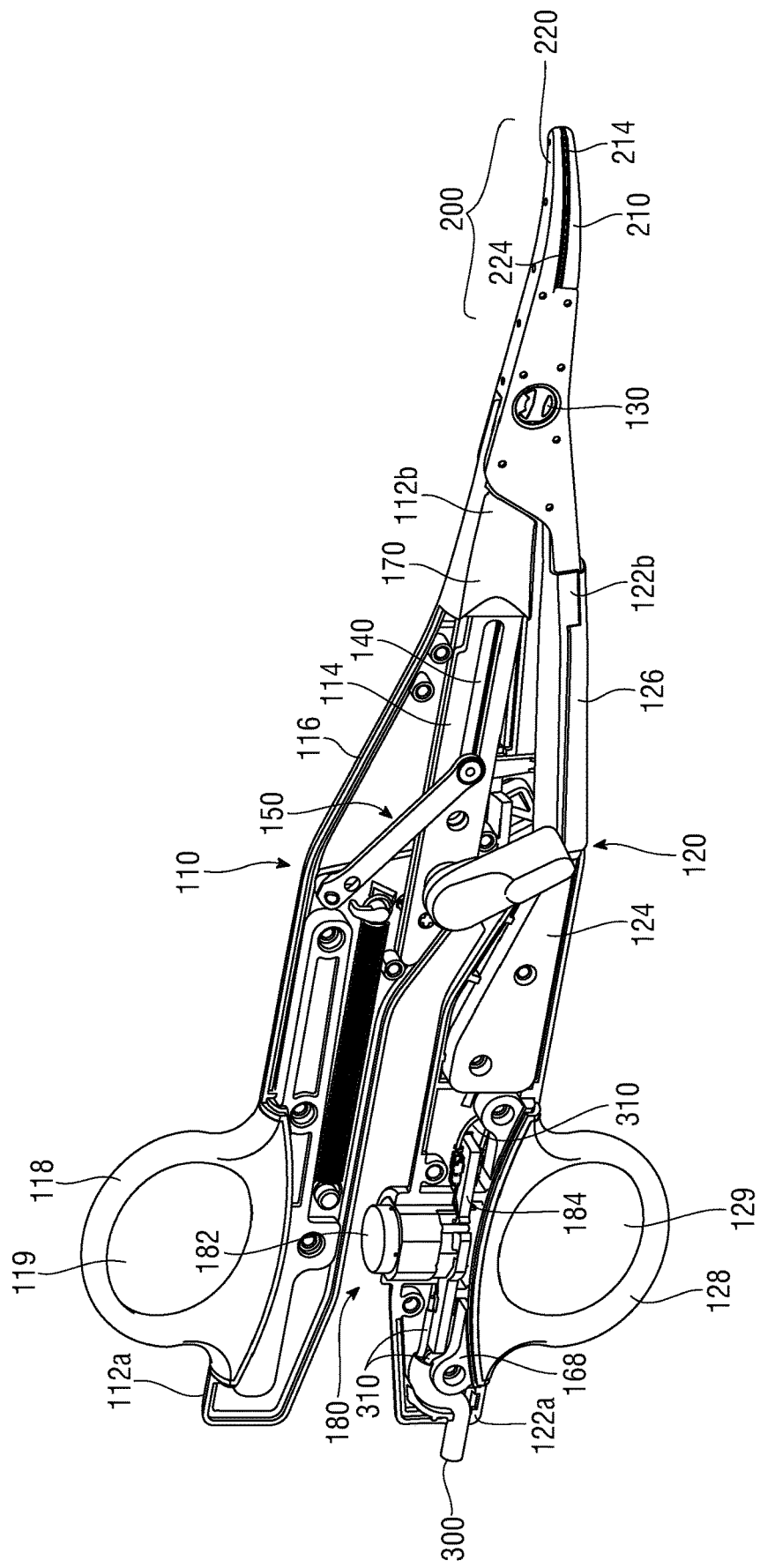
FIG. 2B is a perspective view, from the second side, of the electrosurgical instrument of FIG. 1A with portions of the outer housings of the first and second shaft members removed to illustrate the internal components therein.
Figure 3A:
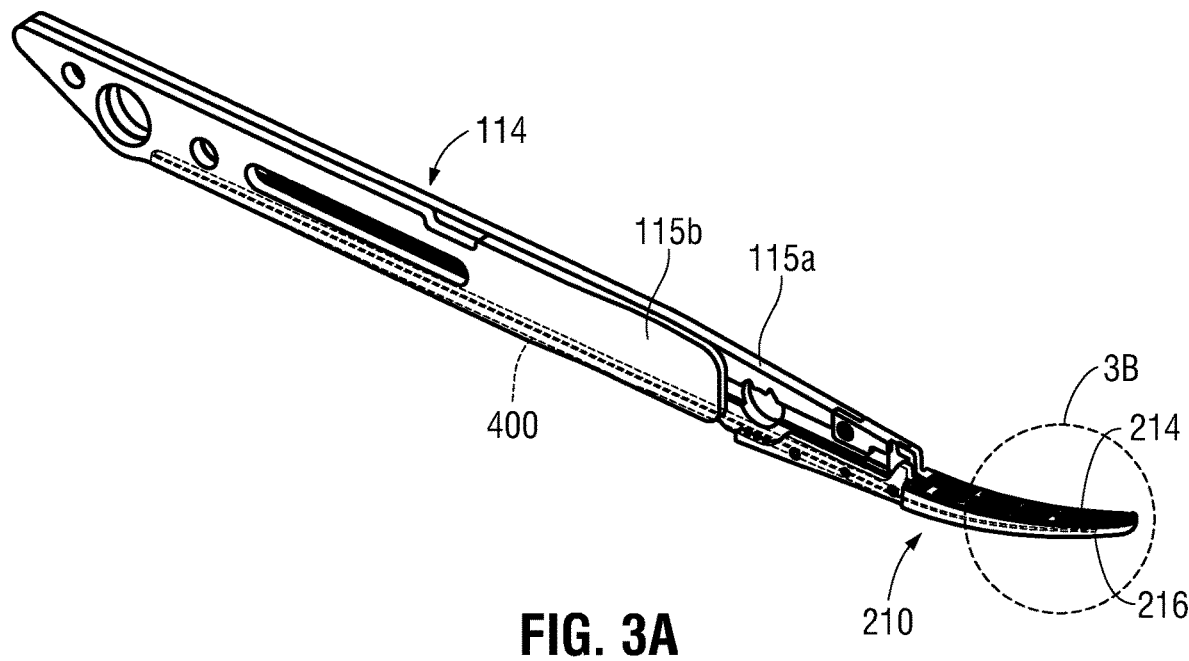
FIG. 3A is a perspective view of the inner frame and jaw member of the first shaft member of the electrosurgical instrument of FIG. 1A.
Figure 3B:
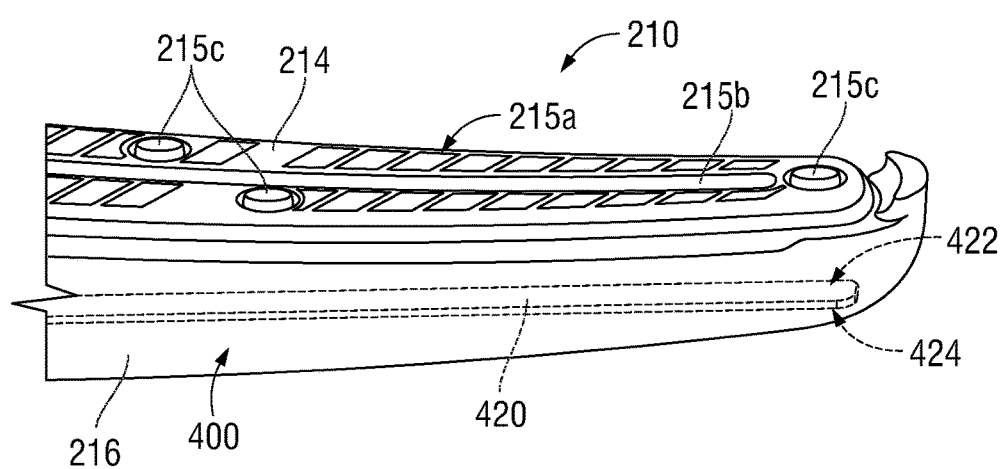
FIG. 3B is an enlarged, perspective view of the area of detail indicated as "3B" in FIG. 3A.

With additional reference to FIGS. 3A and 3B, end effector assembly 200 of instrument 100, as noted above, includes first and second jaw members 210, 220 supported by and extending distally from respective inner frames 114, 124 of shaft members 110, 120, respectively. Alternatively, in embodiments, one or both of jaw members 210, 220 may be formed as a single piece with its respective shaft member 110, 120. Each jaw member 210, 220 includes an electrically-conductive, tissue-contacting plate 214, 224 and an insulative housing 216, 226 surrounding and supporting the respective tissue-contacting plate 214, 224 thereon. Each jaw member 210, 220 further includes a structural jaw support (not shown) secured to the distal end portions of inner frames 114, 124, of shaft members 110, 120, respectively, and extending distally therefrom. Insulative housings 216, 226 are overmolded or otherwise disposed about the structural jaw supports to enclose jaw members 210, 220 and retain tissue-contacting plates 214, 224, respectively, in position thereon. Each tissue-contacting plate 214, 224 defines a tissue-contacting surface 215a (only tissue contacting surface 215a of tissue-contacting plate 214 of jaw member 210 is shown) and a longitudinally-extending knife channel 215b (only knife channel 215b of tissue-contacting plate 214 of jaw member 210 is shown). One or both tissue-contacting plates 214 may include one or more stop members 215c (stop members 215c are only shown disposed on tissue contacting surface 215a of tissue-contacting plate 214 of jaw member 210) associated therewith, e.g., disposed thereon or protruding therethrough, and electrically isolated therefrom, e.g., via forming stop members 215c at least partially from an electrically-insulative material and/or an intermediate insulating material between stop members 215c and tissue-contacting plate 214. Electrical leads 310 (FIG. 2B) are configured to electrically couple to tissue-contacting plates 214, 224 to enable the supply of electrosurgical energy thereto, e.g., upon activation of switch assembly 180.

Referring back to FIGS. 2A and 2B, knife deployment mechanism 150 is coupled to shaft member 110 and generally includes a pair of opposed triggers 152 extending from either side of shaft member 110, first and second linkages 154, 156, and a biasing spring 158. Linkages 154, 156 operably couple triggers 152 with knife 140 such that actuation of either trigger 152 deploys knife 140 from a retracted position, wherein the cutting edge (not shown) of knife 140 is disposed proximally of jaw members 210, 220, to an extended position, wherein knife 140 extends at least partially through knife channels 215b and between tissue-contacting plates 214, 224 of jaw members 210, 220 to cut tissue grasped therebetween. Biasing spring 158 biases knife 140 towards the retracted position.

Knife lockout mechanism 170 works in conjunction with shaft members 110, 120 to inhibit deployment of knife 140 prior to shaft members 110, 120 reaching a sufficiently-closed position corresponding to a sufficiently-approximated position of jaw members 210, 220. Knife lockout mechanism 170 includes a finger 176 extending from shaft member 110. With shaft members 110, 120 disposed in the open position, finger 176 is spaced-apart from outer housing 126 of shaft member 120 such that knife lockout mechanism 170 is maintained in an engaged position engaging knife 140 to inhibit deployment of knife 140. In order to disengage knife lockout mechanism 170 to disengage knife 140 and permit deployment of knife 140, shaft members 110, 120 are sufficiently closed such that a portion of outer housing 126 of shaft member 120 contacts finger 176 of knife lockout 170 and urges finger 176 into housing 116 of shaft member 110 to thereby disengage knife lockout mechanism 170 from knife 140. With knife lockout mechanism 170 disengaged, knife deployment mechanism 150 may be actuated to deploy knife 140 from the retracted position towards the extended position.

With reference to FIG. 2B, switch assembly 180 is disposed on shaft member 120 and generally includes an activation button 182 and a Printed Circuit Board (PCB) 184. Activation button 182 is configured to be contacted by the outer housing 116 of shaft member 110 upon sufficient approximation of shaft members 110, 120 so as to depress activation button 182 and activate switch assembly 180. PCB 184 supports electrical connectors and contacts that, together with electrosurgical cable 300 (FIG. 1A), electrically couple tissue-contacting plates 214, 224 of jaw members 210, 220, switch assembly 180, and the energy source (not shown) with one another. As a result, activation of activation button 182 initiates the supply of energy from the energy source (not shown) to jaw members 210, 220 such that such energy may be conducted through tissue grasped between tissue-contacting plates 214, 224 of jaw members 210, 220 to treat, e.g., seal, tissue.

Figure 4:
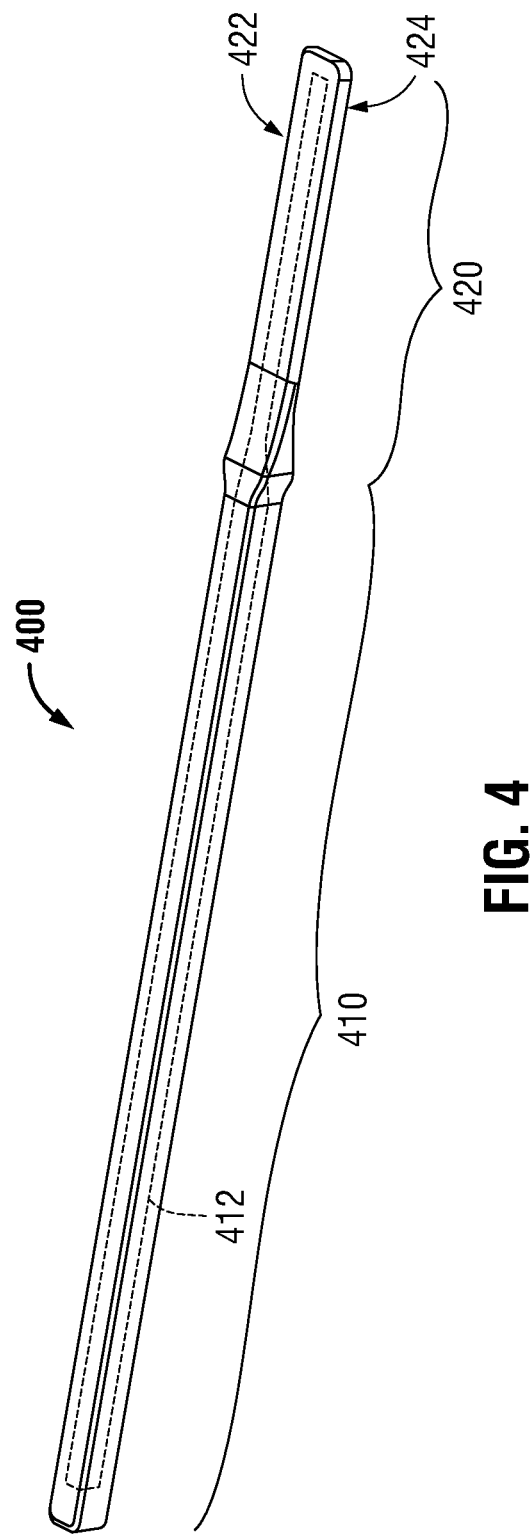
FIG. 4 is a perspective view of the heat pipe of the inner frame and jaw member of the first shaft member of the electrosurgical instrument of FIG. 1A.

Turning to FIGS. 3A-4, as noted above, heat pipe 400 functions as a thermal management feature to facilitate drawing heat proximally away from end effector assembly 200. Heat pipe 400, as also noted above, extends at least partially through shaft member 110 and jaw member 210. Heat pipe 400, more specifically, includes a proximal body portion 410 extending at least partially through shaft member 110 and a distal flattened portion 420 extending at least partially through jaw member 210. Heat pipe 400 is formed from a material with a high thermal conductivity, e.g., copper, polyimide, etc.

Proximal body portion 410 of heat pipe 400 is disposed within outer housing 116 of shaft member 110 and may extend at least partially alongside inner frame 114, underneath inner frame 114, above inner frame 114, within a cut-out defined within inner frame 114, and/or between plates 115a, 115b of inner frame 114. Proximal body portion 410 of heat pipe 400 may contact at least a portion of inner frame 114 to enable inner frame 114 to serve as a heat sink to dissipate heat from heat pipe 400. Proximal body portion 410 of heat pipe 400 extends proximally from the distal end of inner frame 114 and may extend, in embodiments, proximally to or beyond the proximal end of inner frame 114, in other embodiments, proximally at least 75% of the length of inner frame 114, or, in still other embodiments, proximally at least 50% of the length of inner frame 114. Additionally or alternatively, proximal body portion 410 may extend proximally through outer housing 116 of shaft member 110, in embodiments, at least 80% of the length of shaft member 110, in other embodiments, at least 60% of the length of shaft member 110, or, in still other embodiments, at least 40% of the length of shaft member 110. A distal end of proximal body portion 410 may be disposed at the distal end of inner frame 114, at distal end portion 112b of shaft member 110, or at pivot 130.

Proximal body portion 410 of heat pipe 400 defines an internal lumen 412 enclosed therein and extending longitudinally therethrough. A cooling fluid, e.g., water, saline, etc., is disposed within internal lumen 412 to occupy a portion but not entirely fill internal lumen 412. In embodiments, the inner wall of proximal body portion 410 of heat pipe 400 that defines internal lumen 412 includes a wick structure (not shown) configured to exert capillary pressure on the cooling fluid when the cooling fluid is in a liquid phase. The wick structure may be a series of grooves or other suitable structure defined on or within the inner wall of proximal body portion 410.

Distal flattened portion 420 of heat pipe 410 extends distally from proximal body portion 410, e.g., distally from the distal end of inner frame 114, distal end portion 112b of shaft member 110, or pivot 130, at least partially through jaw member 210. More specifically, distal flattened portion 420 extends distally within insulative housing 216 of jaw member 210 along at least a portion of the length of jaw member 210. Distal flattened portion 420 of heat pipe 400 extends, in embodiments, to the distal end of jaw member 210, in other embodiments, at least 75% of the length of jaw member 210, or, in still other embodiments, at least 50% of the length of jaw member 210.

Distal flattened portion 420 defines a spatula-shaped configuration including opposing upper and lower planar surfaces 422, 424, respectively. In other embodiments, upper surface 422 is planer while lower surface 424 is curved, angled, or otherwise configured. Upper surface 422 of distal flattened portion 420 of heat pipe 400 may define a plane disposed in parallel orientation relative to a plane defined by tissue-contacting surface 215a of tissue-contacting plate 214 of jaw member 210. Distal flattened portion 420 may extends distally, in embodiments, to or beyond the distal end of tissue-contacting plate 214 of jaw member 210, in other embodiments, at least 90% of the length of jaw member 210, in yet other embodiments, at least 80% of the length of tissue-contacting plate 214, or, in still other embodiments, at least 70% of the length of tissue-contacting plate 214.

Distal flattened portion 420 may be disposed in direct contact with the underside of tissue-contacting plate 214, may indirectly contact tissue-contacting plate 214 via an intermediate thermally-conductive structure (in embodiments, a thermally-conductive, electrically-insulative structure), or may be disconnected from tissue-contacting plate 214 but thermally coupled thereto, e.g., via the close proximity of distal flattened portion 420 relative to tissue-contacting plate 214 within insulative housing 216 of jaw member 210. In embodiments, distal flattened portion 420 is disposed in contact with the structural jaw support of jaw member 210 in thermal communication therewith to absorb heat therefrom. Further, distal flattened portion 420 may at least partially extend underneath knife channel 215b, along either side of knife channel 215b, and/or through knife channel 215b (without interfering with knife 140 (see FIGS.

2A & 2B) during translation of knife 140 through knife channel 215b). In embodiments, distal flattened portion 420 is bifurcated to surround knife channel 215b on both sides thereof.

Referring to FIG. 4, heat pipe 400 may be formed as a single body including internal lumen 412 extending therethrough and, thereafter, the distal portion of heat pipe 400 may be flattened to define distal flattened portion 420. Other methods of manufacturing heat pipe 400 are also contemplated. Regardless of the method of manufacturing heat pipe 400, lumen 412 may extend at least partially through distal flattened portion 420 and may be occluded within distal flattened portion 420 due to the flattened configuration of distal flattened portion 420 to inhibit fluid flow therethrough. Alternatively, lumen 412 may be constricted, e.g., to define a reduced volume, through distal flattened portion 420 as a result of the flattening of distal flattened portion 420 to limit fluid flow therethrough.

With general reference to FIGS. 1A-4, in use, with tissue grasped between tissue-contacting plates 214, 224 of jaw members 210, 220, shaft members 110, 120 are sufficiently approximated such that shaft member 110 actuates activation button 182 of switch assembly 180 to initiate the supply of electrosurgical energy to tissue-contacting plates 214, 224. The electrosurgical energy is conducted through the tissue grasped between tissue-contacting plates 214, 224 to heat and treat, e.g., seal, the tissue. As the electrosurgical energy is conducted to treat the tissue, jaw members 210, 220 are heated. As the temperature of jaw member 210 increases, the cooling fluid within internal lumen 412 of heat pipe at distal flattened portion 420 of heat pipe 400 and/or at the distal end portion of proximal body portion 410 of heat pipe 400 absorbs heat from jaw member 210, thereby transitioning the cooling fluid from a liquid phase to a vapor phase. The cooling fluid, in the vapor phase, travels proximally through heat pipe 500 away from jaw member 210. Once sufficiently displaced from jaw member 210 and the elevated temperature thereof, the cooling fluid releases the absorbed heat through proximal body portion 410 of heat pipe 400. As the cooling fluid releases the absorbed heat, the cooling fluid returns from the vapor phase to the liquid phase and thus returns distally towards jaw member 210 to repeat the cycle. In this manner, heat is drawn away from jaw member 210 (and, thus, end effector assembly 200) and is dissipated within shaft member 110. In embodiments, it is contemplated that heat pipe 400 cool jaw member 210 down to a temperature of about 60° C. or below, e.g., from 90° C.

In embodiments, heat pipe 400 may define a length relative to a length of tissue-contacting plate 214 of jaw member 210 to facilitate cooling. More specifically, the heat pipe length to tissue-contacting plate length ratio may be, in embodiments, from 1:1 to 2:1; in other embodiments, at least 6:1; in other embodiments, at least 9:1; and in still other embodiments, at least 12:1. In percentage terms, the tissue-contacting plate length may be, in embodiments, from 6% to 12% of the length of the heat pipe; in other embodiments, at least 60% of the length of the heat pipe; and in still other embodiments, at least 80% of the length of the heat pipe.

In embodiments, tissue-contacting plate 214 may define an exposed surface area relative to a maximum, minimum, or average cross-sectional area of heat pipe 400 to facilitate cooling. More specifically, the exposed tissue-contacting plate surface area to heat pipe cross-sectional area ratio may be, in embodiments, from 3:1 to 4:1; in other embodiments, from 20:1 to 35:1; in still other embodiments, from 3:1 to 35:1. In percentage terms, the heat pipe cross-sectional area may be from 2% to 5% of the exposed surface area of the tissue-contacting plate; in other embodiments, from 20-35% of the exposed surface area of the tissue-contacting plate; and in still other embodiments, from 2-35% of the exposed surface area of the tissue-contacting plate.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical instrument, comprising:
   at least one shaft member;
   an end effector assembly extending distally from the at least one shaft member, the end effector assembly including first and second jaw members, each of the first and second jaw members including an electrically-conductive tissue-contacting surface, at least one of the first or second jaw members movable relative to the other about a pivot between a spaced-apart position and an approximated position for grasping tissue between the electrically-conductive tissue-contacting surfaces; and
   a heat pipe including a proximal body portion having a first cross-sectional configuration and a flattened distal portion having a second cross-sectional configuration that is flattened relative to the first cross-sectional configuration, the proximal body portion extending through at least 40% of the at least one shaft member, and the flattened distal portion extending through at least a substantial portion of the first jaw member, the heat pipe defining an internal lumen configured to circulate a cooling fluid between the proximal body portion and the flattened distal portion to facilitate drawing heat proximally from the end effector assembly,
   wherein the second cross-sectional configuration constricts the internal lumen in the flattened distal portion of the heat pipe to reduce or inhibit flow of the cooling fluid through the flattened distal portion relative to flow of the cooling fluid through the proximal body portion.

2. The electrosurgical instrument according to claim 1, wherein the distal flattened portion of the heat pipe defines a spatula-shaped configuration.

3. The electrosurgical instrument according to claim 1, wherein the distal flattened portion of the heat pipe includes an upper surface defining a plane disposed in parallel orientation relative to and underneath a plane defined by the electrically-conductive tissue-contacting surface of the first jaw member.

4. The electrosurgical instrument according to claim 1, wherein the at least one shaft member includes an inner frame and an outer housing, and wherein the proximal body portion of the heat pipe extends through the outer housing and at least one of: alongside, above, below, or through the inner frame.

5. The electrosurgical instrument according to claim 1, wherein a length of the distal flattened portion of the heat pipe is configured in accordance with a length of the electrically-conductive tissue-contacting surface of the first jaw member.

6. The electrosurgical instrument according to claim 1, wherein a length of the heat pipe is configured in accordance with a length of the electrically-conductive tissue-contacting surface of the first jaw member.

7. The electrosurgical instrument according to claim 1, wherein a cross-sectional area of the heat pipe is configured in accordance with an exposed surface area of the electrically-conductive tissue-contacting surface of the first jaw member.

8. The electrosurgical instrument according to claim 1, wherein the flattened distal portion of the heat pipe is disposed proximate the electrically-conductive tissue-contacting surface of the end effector assembly.

9. An electrosurgical instrument, comprising:
first and second shaft members movable relative to one another about a pivot;
first and second jaw members extending distally from the first and second shaft members, respectively, each of the first and second jaw members including an electrically-conductive tissue-contacting surface, wherein movement of the first and second shaft members relative to one another from an open position to a closed position moves the first and second jaw members relative to one another from a spaced-apart position to an approximated position for grasping tissue between the electrically-conductive tissue-contacting surfaces; and
a heat pipe including a proximal body portion having a first cross-sectional configuration and a flattened distal portion having a second cross-sectional configuration that is flattened relative to the first cross-sectional configuration, the proximal body portion extending through at least 40% of the first shaft member, and the flattened distal portion extending through at least a substantial portion of the first jaw member, the heat pipe defining an internal lumen configured to circulate a cooling fluid between the proximal body portion and the flattened distal portion to facilitate drawing heat proximally from the first and second jaw members,
wherein the second cross-sectional configuration constricts the internal lumen in the flattened distal portion of the heat pipe to reduce or inhibit flow of the cooling fluid through the flattened distal portion relative to flow of the cooling fluid through the proximal body portion.

10. The electrosurgical instrument according to claim 9, wherein the distal flattened portion of the heat pipe defines a spatula-shaped configuration.

11. The electrosurgical instrument according to claim 9, wherein the distal flattened portion of the heat pipe includes an upper surface defining a plane disposed in parallel orientation relative to and underneath a plane defined by the electrically-conductive tissue-contacting surface of the first jaw member.

12. The electrosurgical instrument according to claim 9, wherein the first shaft member includes an inner frame and an outer housing, and wherein the proximal body portion of the heat pipe extends through the outer housing and at least one of: alongside, above, below, or through the inner frame.

13. The electrosurgical instrument according to claim 9, wherein a length of the distal flattened portion of the heat pipe is configured in accordance with a length of the electrically-conductive tissue-contacting surface of the first jaw member.

14. The electrosurgical instrument according to claim 9, wherein a length of the heat pipe is configured in accordance with a length of the electrically-conductive tissue-contacting surface of the first jaw member.

15. The electrosurgical instrument according to claim 9, wherein a cross-sectional area of the heat pipe is configured in accordance with an exposed surface area of the electrically-conductive tissue-contacting surface of the first jaw member.

16. The electrosurgical instrument according to claim 9, wherein the flattened distal portion of the heat pipe is disposed proximate the electrically-conductive tissue-contacting surface of the first jaw member.

17. An electrosurgical instrument, comprising:
at least one shaft member;
an end effector assembly extending distally from the at least one shaft member, the end effector assembly including first and second jaw members, each of the first and second jaw members including an electrically-conductive tissue-contacting surface, at least one of the first or second jaw members movable relative to the other about a pivot between a spaced-apart position and an approximated position for grasping tissue between the electrically-conductive tissue-contacting surfaces; and
a heat pipe including a proximal body portion having a first cross-sectional configuration and a flattened distal portion having a second cross-sectional configuration that is flattened relative to the first cross-sectional configuration, the proximal body portion extending through at least 40% of the at least one shaft member, and the flattened distal portion extending substantially a length of the electrically-conductive tissue contacting surface through the first jaw member, the heat pipe defining an internal lumen configured to circulate a cooling fluid between the proximal body portion and the flattened distal portion to facilitate drawing heat proximally from the end effector assembly,
wherein the second cross-sectional configuration constricts the internal lumen in the flattened distal portion of the heat pipe to reduce or inhibit flow of the cooling fluid through the flattened distal portion relative to flow of the cooling fluid through the proximal body portion.

18. The electrosurgical instrument according to claim 17, wherein the distal flattened portion of the heat pipe defines a spatula-shaped configuration.

19. The electrosurgical instrument according to claim 17, wherein the distal flattened portion of the heat pipe includes an upper surface defining a plane disposed in parallel orientation relative to and underneath a plane defined by the electrically-conductive tissue-contacting surface of the first jaw member.

20. The electrosurgical instrument according to claim 17, wherein the at least one shaft member includes an inner frame and an outer housing, and wherein the proximal body portion of the heat pipe extends through the outer housing and at least one of: alongside, above, below, or through the inner frame.

* * * * *